(12) United States Patent
Galada et al.

(10) Patent No.: US 11,317,989 B2
(45) Date of Patent: May 3, 2022

(54) DENTAL BITE BLOCK

(71) Applicants: Michael Galada, Las Vegas, NV (US); Ian P Smith, Las Vegas, NV (US)

(72) Inventors: Michael Galada, Las Vegas, NV (US); Ian P Smith, Las Vegas, NV (US)

(*) Notice: Subject to any disclaimer, the term of this patent is extended or adjusted under 35 U.S.C. 154(b) by 170 days.

(21) Appl. No.: 16/884,199

(22) Filed: May 27, 2020

(65) Prior Publication Data

US 2021/0369411 A1    Dec. 2, 2021

(51) Int. Cl.
*A61C 5/90* (2017.01)
*A61B 1/24* (2006.01)

(52) U.S. Cl.
CPC . *A61C 5/90* (2017.02); *A61B 1/24* (2013.01)

(58) Field of Classification Search
CPC .... A61C 5/90; A61B 1/24; A46B 9/04; A46B 2200/1066; A46B 9/045; A46B 5/0008; A46B 5/0012
See application file for complete search history.

(56) References Cited

U.S. PATENT DOCUMENTS

| | | | |
|---|---|---|---|
| 3,722,101 A | 3/1973 | Via | |
| 5,009,595 A | 4/1991 | Osborn | |
| 6,241,521 B1 | 6/2001 | Garrison | |
| 9,021,992 B1 * | 5/2015 | Cogley | A61D 5/00 119/831 |
| 2004/0033468 A1 * | 2/2004 | Fischer | A61C 5/90 433/140 |
| 2006/0272113 A1 * | 12/2006 | Cato | A46B 9/04 15/106 |
| 2010/0291503 A1 * | 11/2010 | Shih | A61B 90/16 433/31 |
| 2020/0383560 A1 * | 12/2020 | Day | A61C 5/90 |

* cited by examiner

*Primary Examiner* — Jacqueline T Johanas
*Assistant Examiner* — Lina Faraj
(74) *Attorney, Agent, or Firm* — Argus Intellectual Enterprise; Daniel Enea; Jordan Sworen

(57) ABSTRACT

A dental bite block is provided. The dental bite block includes a body having a first end and a second end, an outer sidewall, and an inner sidewall. The body comprises an upper biting surface positioned within an upper channel and a lower biting surface within a lower channel. The outer sidewall and the inner sidewall extend past the upper and lower biting surfaces and define the upper channel and the lower channel, respectively. The upper channel and the lower channel are each able to receive a row of teeth therein. The dental bite block prevents the biting down and provides safe access to the interior of the mouth. A handle extends from the bite block and is releasably tethered to a toothbrush such that the teeth of the subject may be brushed when the teeth are received within the mouth of the subject.

17 Claims, 10 Drawing Sheets

DENTAL BITE BLOCK

BACKGROUND OF THE INVENTION

The present invention relates to a dental bite block and method. More specifically, the present invention relates to a dental bite block that allows subjects that are unable to perform oral hygiene on themselves in a conventional manner, whether it be due to their age or physical capabilities, to receive oral home care. Additionally, the dental bite block includes a tooth brushing instrument that is attached thereto. The dental bite block ensures that subjects and dentists alike can perform dental hygiene procedures, such as teeth brushing, and reduce the risk of the subject inadvertently biting an assisting hand.

Dental procedures often require a dentist and/or dental hygienist to work within the subject's mouth under limited access and lighting conditions. For example, during dental procedures that require access to certain teeth and areas of the mouth, the dentist's hand is at risk of being bit by the subject. In addition, some procedures require the subject's mouth to be open for substantial periods of time. For some subjects, whether it be due to their age or physical capabilities, may not be capable of maintaining such a position unassisted.

Dental mouth props, or bite blocks, are devices which are inserted into a subject's mouth between the upper and lower teeth to keep the mouth opened in a fixed position. In typical use, the teeth on one side will be contacting the bite block and the teeth on the opposite side will be more accessible. These bite blocks are mostly used to enhance the efficiency of the dental practitioner by reducing the risk of the patient inadvertently biting the practitioner's hands.

Bite blocks are even more useful during long dental appointments when the patient's jaw muscles fatigue. The bite block allows the patient to relax the muscles and teeth on the block, which does the work in keeping the mouth open.

In some examples of bite blocks, the dentist may find it necessary to reposition the bite block during the procedure due to patient's discomfort or to gain access to additional mouth space. However, this inconveniences the dentist and the subject as the procedure may need to take additional time to complete the procedure. These known dental bite blocks do not address the home and professional needs as they are difficult to position and retain in the mouth.

In view of the above concerns, it is desirable to provide an embodiment of the dental bite block that eliminates the problems of known bite blocks. The present dental bite block provides a safer subject and user experience and provides increased stability when received within the mouth. Further, the dental bite block may provide an attached toothbrush that allows for a secure connection between the connecting strap and the replaceable toothbrush, or other dental instrument.

In light of the devices disclosed in the known art, it is submitted that the present invention substantially diverges in design elements and methods from the known art and consequently it is clear that there is a need in the art for an improvement for a dental bite block and method of use. In this regard the instant invention substantially fulfills these needs.

SUMMARY OF THE INVENTION

In view of the foregoing disadvantages inherent in the known types of dental bite blocks now present in the known art. The present invention provides a new dental bite block and method of use, wherein the same can be utilized for professional and home use.

It is an objective of the present invention to provide a dental bite block configured to position the mouth of the subject in a relaxed and desirable open position for facilitating access to the subject's mouth.

It is another objective of the present invention to provide a dental bite block that provides a flexible and modestly compressible body. In this way, the biting down of the bite block prevents damage or injury to the subject while ensuring that the subject's mouth remains in an open position.

It is yet another objective of the present invention to provide a dental bite block having an attached toothbrush that allows for a secure connection between the connecting strap and the replaceable toothbrush, or other dental instrument.

It is another objective of the present invention to provide a dental bite block that is adapted for use on either side of a subject's mouth without modification to the dental bite block.

It is yet another objective of the present invention to provide a dental bite block that is adapted for use with subjects of various ages and mouth sizes.

It is another object of the present invention to provide a toothbrush that is releasably connected to a handle of the bite block such that the toothbrush remains in arms reach from the subject, or a person assisting the subject.

It is another object of the present invention to provide a key that allows for selective replacement of the toothbrush, wherein the key is housed within the handle.

It is yet another objective of the present invention to provide a dental bite block comprising a body having a first end and a second end, wherein an outer sidewall and an inner sidewall are disposed on opposing sides thereof. The body comprises an upper biting surface positioned within an upper channel and a lower biting surface and a lower channel, wherein the outer sidewall and the inner sidewall extend past the upper and lower biting surfaces and define the upper channel and the lower channel, respectively. The upper channel and the lower channel are each adapted to receive a row of teeth therein and the body comprises a front face at the first end thereof, wherein the front face extends between the upper biting surface and the lower biting surface.

It is therefore an object of the present invention to provide a new and improved dental bite block that has all of the advantages of the known art and none of the disadvantages.

Other objects, features and advantages of the present invention will become apparent from the following detailed description taken in conjunction with the accompanying drawings.

BRIEF DESCRIPTIONS OF THE DRAWINGS

Although the characteristic features of this invention will be particularly pointed out in the claims, the invention itself and manner in which it may be made and used may be better understood after a review of the following description, taken in connection with the accompanying drawings wherein like numeral annotations are provided throughout.

DETAILED DESCRIPTION OF THE INVENTION

Figure 1:
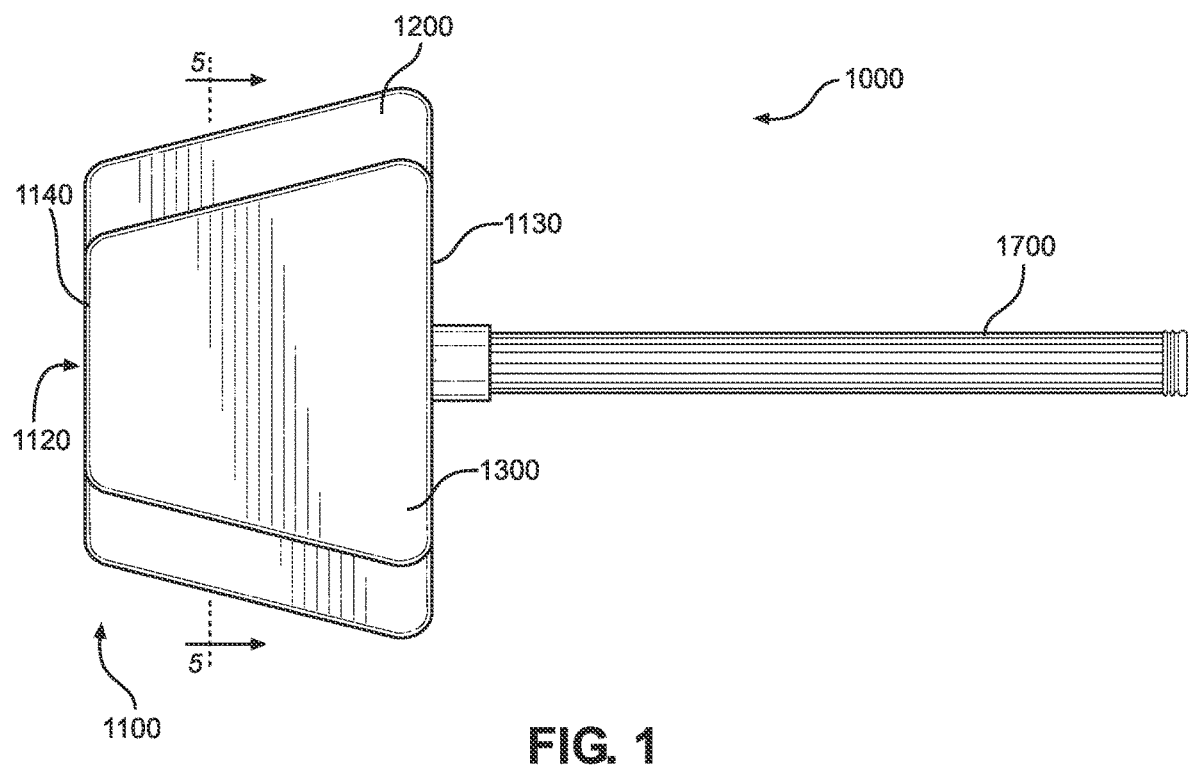
FIG. 1 shows a side view of an embodiment of the dental bite block.

Reference is made herein to the attached drawings. Like reference numerals are used throughout the drawings to depict like or similar elements of the dental bite block and method. For the purposes of presenting a brief and clear description of the present invention, the preferred embodiment will be discussed as used for insertion into a subject's mouth between the upper and lower teeth to keep the mouth opened in a fixed position. The figures are intended for representative purposes only and should not be considered to be limiting in any respect. Furthermore, the described features, structures, or characteristics may be combined in any suitable manner in one or more embodiments. In the following description, numerous specific details are provided to give a thorough understanding of embodiments.

Reference will now be made in detail to the exemplary embodiment (s) of the invention. References to "one embodiment," "at least one embodiment," "an embodiment," "one example," "an example," "for example," and so on indicate that the embodiment(s) or example(s) may include a feature, structure, characteristic, property, element, or limitation but that not every embodiment or example necessarily includes that feature, structure, characteristic, property, element, or limitation. Further, repeated use of the phrase "in an embodiment" does not necessarily refer to the same embodiment.

Figure 2:
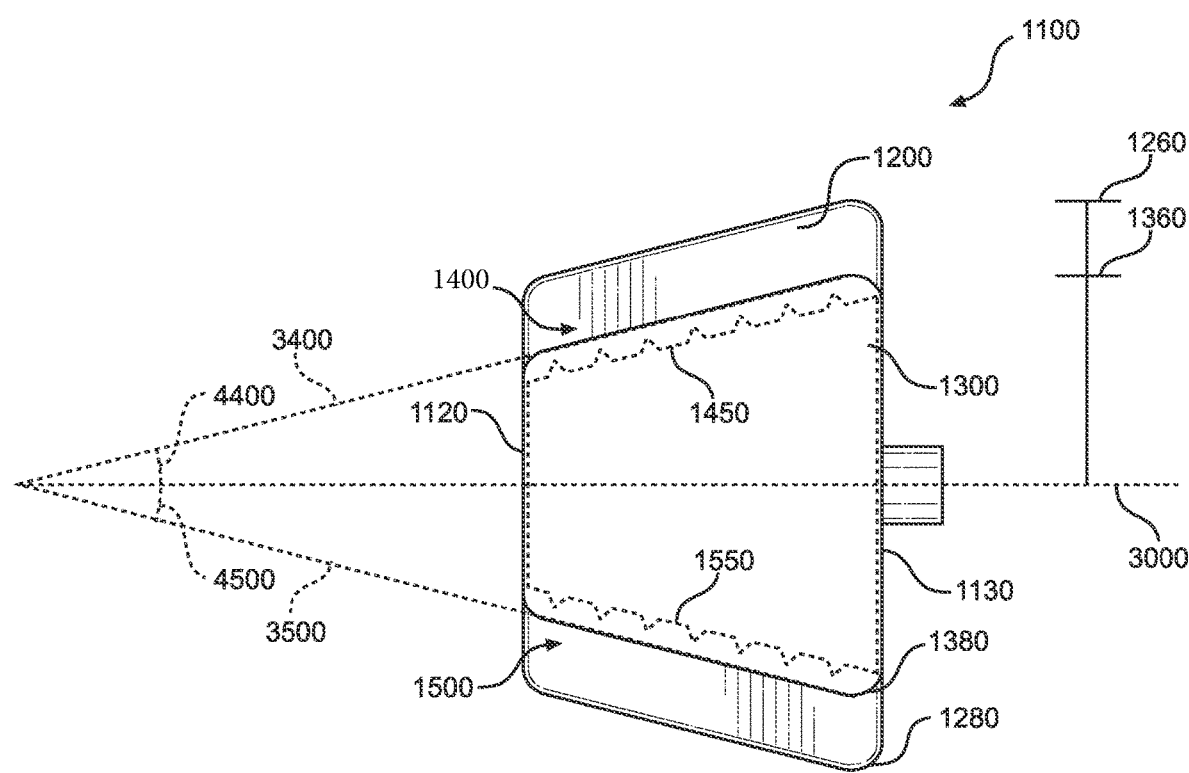
FIG. 2 shows another side view of one embodiment of the body of the dental bite block.

Referring now to FIGS. 1 and 2, there are shown side views of an embodiment of the dental bite block. The dental bite block 1000 provides safe access to the interior of the mouth by preventing the biting down of the subject on to a hand of a dental professional or other care giver. The dental bite block 1000 comprises a body 1100 having a first end 1120 and a second end 1130 disposed opposite therefrom. An outer sidewall 1200 and an inner sidewall 1300 are positioned on opposing lateral sides of the body 1100 and define the lateral-most boundary of the dental bite block 1000. The body 1100 comprises an upper biting surface 1450 positioned within an upper channel 1400 and a lower biting surface 1550 within a lower channel 1500.

In the shown embodiment, the outer sidewall 1200 and the inner sidewall 1300 extend past the upper and lower biting surfaces 1450, 1550 and define the upper channel 1400 and the lower channel 1500, respectively. In this way, the upper and the lower channel 1400, 1500 are each adapted to securely receive a row of teeth therein.

In the illustrated embodiment, the body 1100 comprises a solid, monolithic member that extends from the first end 1120 to the second end 1130. The body 1100 comprises a front face 1140 at the first end 1120 thereof, wherein the front face 1140 extends between the upper biting surface 1450 and the lower biting surface 1550. The front face 1140 terminates at a vertical plane that is perpendicular to a longitudinal axis that extends between the first and second end 1120, 1130 of the body. The front face 1140 is flush and coplanar with the front of the outer and inner sidewalls 1200, 1300, respectively.

In the shown embodiment, the upper channel 1400 and the lower channel 1500 are open at the first end 1120 and the second end 1230, respectively. In this way, the subject's row of teeth may be positioned and repositioned within the corresponding channels 1400, 1500. Moreover, an exterior side 1250 of the outer sidewall 1200 is planar and continuous entirely thereacross. In this way, the outer sidewall 1200 is adapted to fit comfortably between a row of teeth of a subject and the interior side of the mouth. In an alternative embodiment, the channels 1400, 1500 are curved inwards to fit within rows of teeth having various shape.

Referring specifically to FIG. 2, the upper biting surface and the lower biting surface 1450, 1550 are inclined towards the first end 1120. The upper biting surface and the lower biting surface 1450, 1550 are positioned in such away as to engage with each tooth of the subject and to maintain the mouth in a desired open position. The outer sidewall 1200 comprises a first height 1260 greater than a second height 1360 of the inner sidewall 1300 at a same vertical cross section along a longitudinal axis of the body 3000. In this way, the outer sidewall 1200 is always protruding past the inner sidewall 1300 and is adapted to be positioned against an exterior side of the row of teeth when the row of teeth are received within the respective channels 1400, 1500.

In the shown embodiment, the outer and the inner sidewall 1200, 1300 are inclined towards the first end 1120 and the body 1100 is thicker at the second end 1130 thereof than at the first end 1120. The taper of the outer and the inner sidewall 1200, 1300 allows for the outer sidewall to shoulder the row of teeth when the row of teeth is received within the respective upper and lower channels 1400, 1500. Furthermore, the outer sidewall and the inner sidewall 1200, 1300 are inclined at a uniform slope to provide maximum comfort to the subject and to allow consistent pressure to be exerted across the entirety of the upper and lower biting surfaces 1450, 1550.

In one embodiment, the dental bite block 1000 is symmetrical about a horizontal plane disposed on a longitudinal axis of the body 3000 such that wherein a longitudinal axis of the upper channel 3400 and a longitudinal axis of the lower channel 3500 converge at an intersection point 3600 disposed on the horizontal plane. The upper channel 1400 and the lower channel 1500 each forms an acute angle 4400, 4500 relative to the longitudinal axis of the body 3000. In one embodiment the acute angles 4400, 4500 are each between fifteen and thirty degrees. In alternative embodiments, the acute angles 4400, 4500 are between 0 and 90 degrees.

In the illustrated embodiment, the outer sidewall and the inner sidewall 1200, 1300 each comprise rounded corners 1280, 1380. The rounded corners 1280, 1380 prevent puncturing and discomfort when the dental bite block 1000 is positioned within the mouth.

Figure 3:
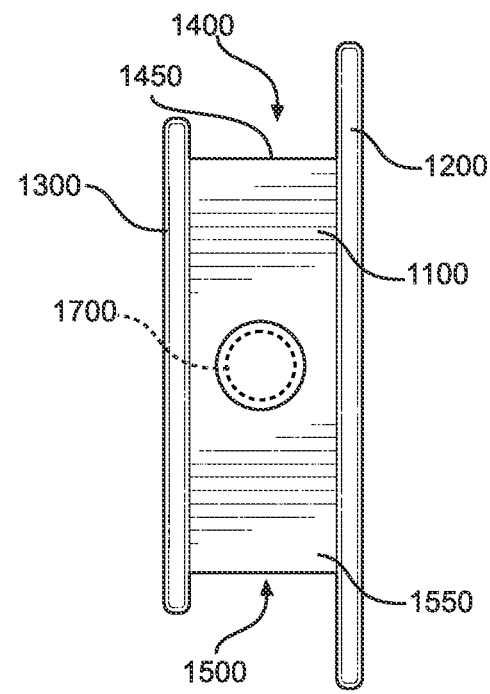
FIG. 3 shows a rear end view of an embodiment of the dental bite block.

In some embodiments, as shown in FIGS. 1 and 3, a handle 1700 extend from the second end 1130 of the body 1100. The handle 1700 comprises a generally tubular member that is adapted for gripping. The handle 1700 is disposed centrally on the body 1100, such that the handle 1700 is oriented along the longitudinal axis.

Figure 4:
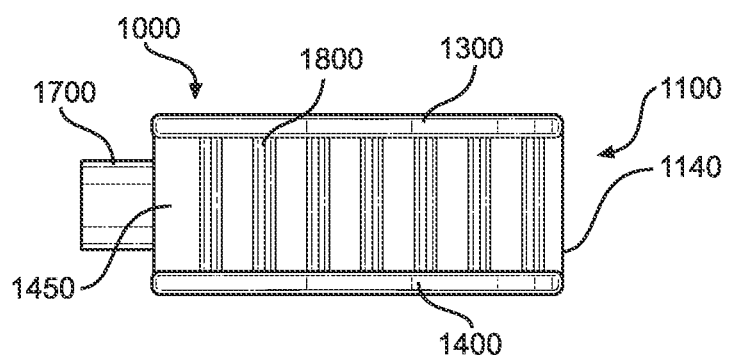
FIG. 4 shows a top view of an embodiment of the dental bite block.
Figure 5:
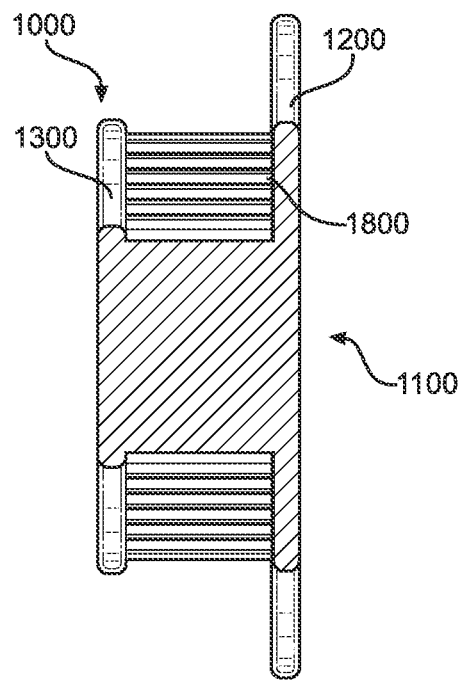
FIG. 5 shows a cross sectional view of an embodiment of the dental bite block taken along lines 5-5 of FIG. 1.

Referring now to FIGS. 4 and 5, there is shown a top view of an embodiment of the dental bite block and a cross sectional view of an embodiment of the dental bite block taken along lines 5-5 of FIG. 1, respectively. The upper and lower biting surfaces 1450, 1550 of the dental bite block 1000 comprise one or more ribs 1800 adapted for aiding traction on the dental bite block 1000 by the upper and lower teeth of the subject. In the shown embodiment, the ribs 1800 comprise a plurality of ribs oriented perpendicular to the longitudinal axis of the upper channel and the lower channel, respectively. Each rib is spaced at a fixed interval to each adjacent rib 1800. In one embodiment, the space between a pair of adjacent ribs 1800 is sized to fit a width of a tooth therein. In this way, the upper and lower biting surfaces 1450, 1550 provide additional contact points with the subject and assists with the securement of the dental bite block 1000 to the subject's mouth.

In one embodiment, wherein a width between the outer and inner sidewalls is uniform, and wherein there is a uniform height difference between sidewalls at a same cross section along a longitudinal axis of the body In one embodiment, the body 1100 comprises silicon, such as food grade silicon. The silicon body 1100 provides a degree of compressibility and flexibility so as to allow a user biting down on the dental bite block 1000 to slightly compress. The compression also allows for greater retention of the dental bite block 1000 in the subject's mouth by allowing the subject to exert a higher biting force to the dental bite block 1000. Moreover, the silicon body 1100 does not damage the teeth or gums of the subject.

Figure 7:
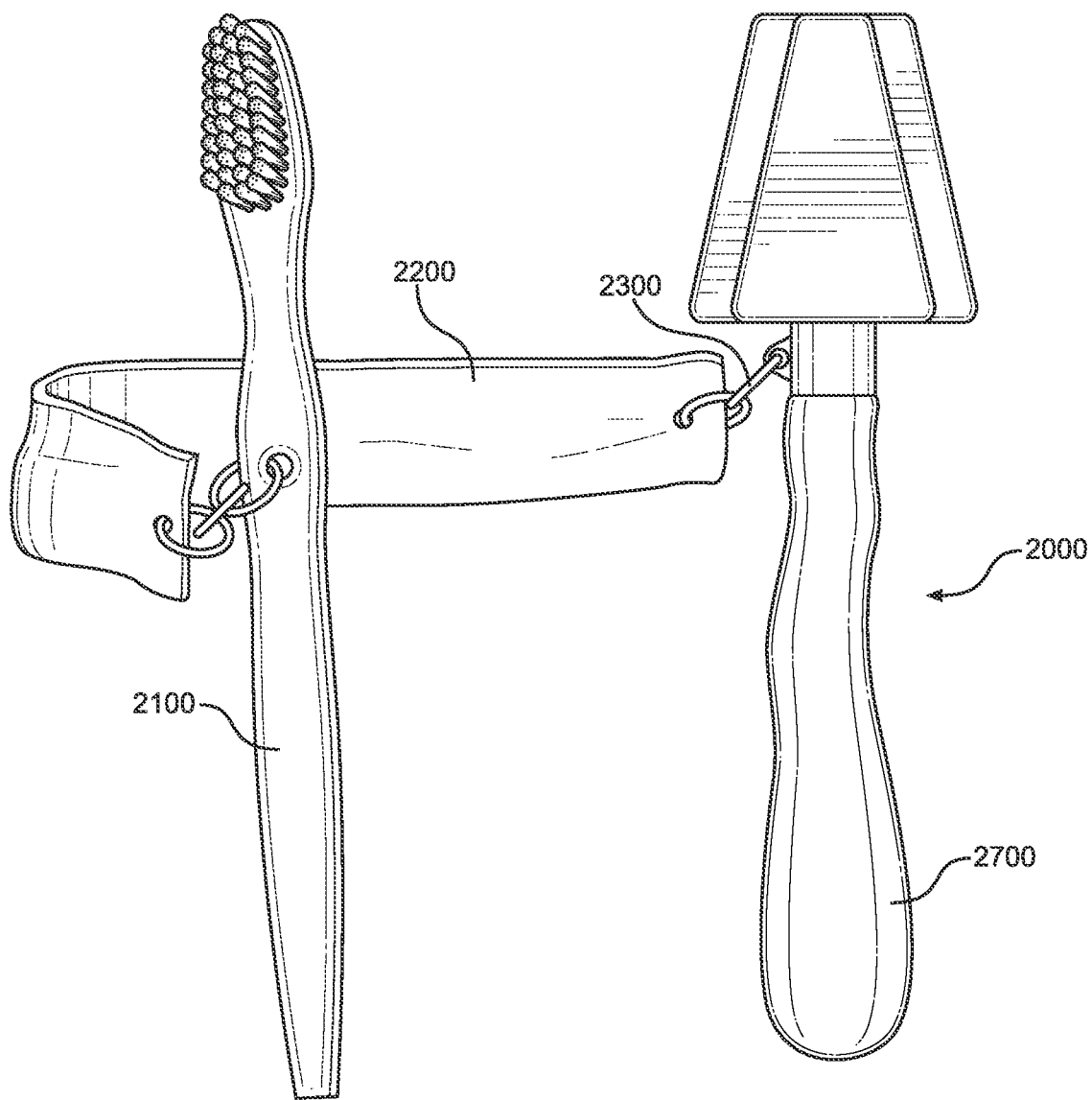
FIG. 7 shows a perspective view of a second embodiment of the dental bite block with a toothbrush attached.

In some embodiments, as shown in FIG. 7, the body of the dental bite block 2000 comprises a core being a distinct material from the exterior. The core may be formed of metal, plastic, or any other rigid material.

Figure 6:
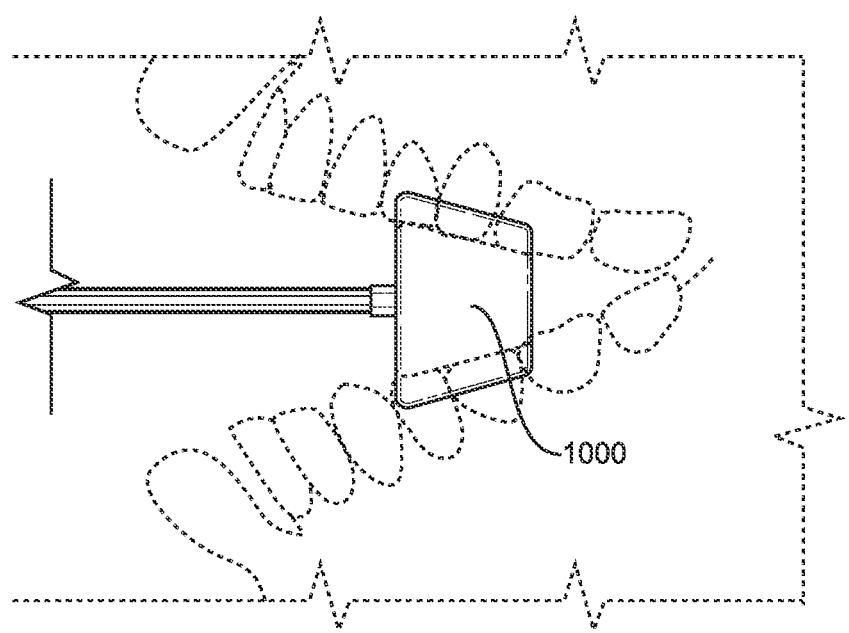
FIG. 6 shows a side view of an embodiment of the dental bite block received within the subject's mouth.

Referring now to FIG. 6, there is shown an embodiment of the dental bite block received within the subject's mouth. In one exemplary use, the subject inserts the dental bite block 1000 into their open mouth such that the upper row of teeth is positioned within the upper channel and engages the upper biting surface, and that the lower row of teeth is positioned within the lower channel and engages the lower biting surface. In the shown embodiment, the first end of the dental bite block 1000 is positioned at the premolars. However, in alternative embodiments, the dental bite block 1000 is adapted to engage with the molars.

In the shown embodiment, the outer sidewall comprises a first height greater than a second height of the inner sidewall at a same cross section along a longitudinal axis of the body. In this way, the outer sidewall abuts the exterior side of the teeth and acts to guide the teeth to be received within the respective upper and lower channel.

In the shown embodiment, the upper channel and the lower channel each form an acute angle relative to a longitudinal axis of the body, wherein the acute angle is between fifteen and thirty degrees. However, in alternative embodiments, the dental bite block may comprise any acute angle.

Referring now to FIG. 7, there is shown a second embodiment of the dental bite block with a toothbrush attached. In the shown embodiment, the dental bite block 2000 comprises a similarly shaped body having a first end and a second end, wherein an outer sidewall and an inner sidewall are disposed on opposing sides thereof. The longitudinal dimension of the shown dental bite block 2000 is greater than that of the dental bite block 1000 shown in FIG. 1. In one embodiment, the dental bite block comprises a total length along the longitudinal axis of 55 mm. This embodiment is adapted for use by elderly and special-needs subjects that are unable to brush their own teeth.

In the shown embodiment, a fastener 2300 is disposed at the second end of the dental bite block 2000. A toothbrush 2100, or other dental instrument, is operably connected to the dental bite block 2000 via a tether 2200. The tether 2200 is affixed to the dental bite block 2000 such that, in use, the toothbrush 2100 and tether 2200 do not interfere with the engagement of the teeth relative to the upper and lower channels, respectively. In the shown embodiment, the handle 2700 is tubular member that extend from the dental bite block 2000. The handle 2700 comprises an ergonomic design and includes curvature that is adapted to conform to the handler's grip.

In the shown embodiment, the fastener 2300 is adapted to removably secure the handle 2700 thereto. The fastener 2300 is removable so that accidental pulling of the toothbrush while the dental bite block 2000 is positioned within the subject's mouth will decouple the toothbrush and prevent injury. As shown, the tether 2200 may be a fabric. In alternative embodiments, the tether 2200 may be a wire, rope, and the like. In another embodiment, the dental bite block 2000 is removably affixed to the tether 2200 via a clasp fastener 2300.

In the shown embodiment, the toothbrush 2100 comprises a handle and a head having bristles disposed on a first side and oriented in a similar direction. The toothbrush 2100 is connected to the tether 2200 via a fastener that engages an aperture of the toothbrush 2100 and the tether 2200. In one embodiment, the toothbrush 2100 comprises bristles disposed on the head and located on opposing sides thereof.

In one embodiment, the dental bite block comprises a front face having a height of 6 mm between the upper and lower biting surfaces, the outer and inner sidewall have a length of 24 mm between the first end and the second end, the body is 21 mm at the second end between the upper and lower biting surfaces, and the height of the outer sidewall at the second end is 40 mm.

In one embodiment, the dental bite block comprises an upper and lower channel each having a width of 9-10 mm between the outer sidewall and the inner sidewall.

In one embodiment, the dental bite block comprises an upper and lower channel having a height of 9 mm between the upper and lower biting surfaces respectively and the outer sidewall, and a height of 3.5 mm between the upper and lower biting surfaces respectively and the inner sidewall.

Figure 8:
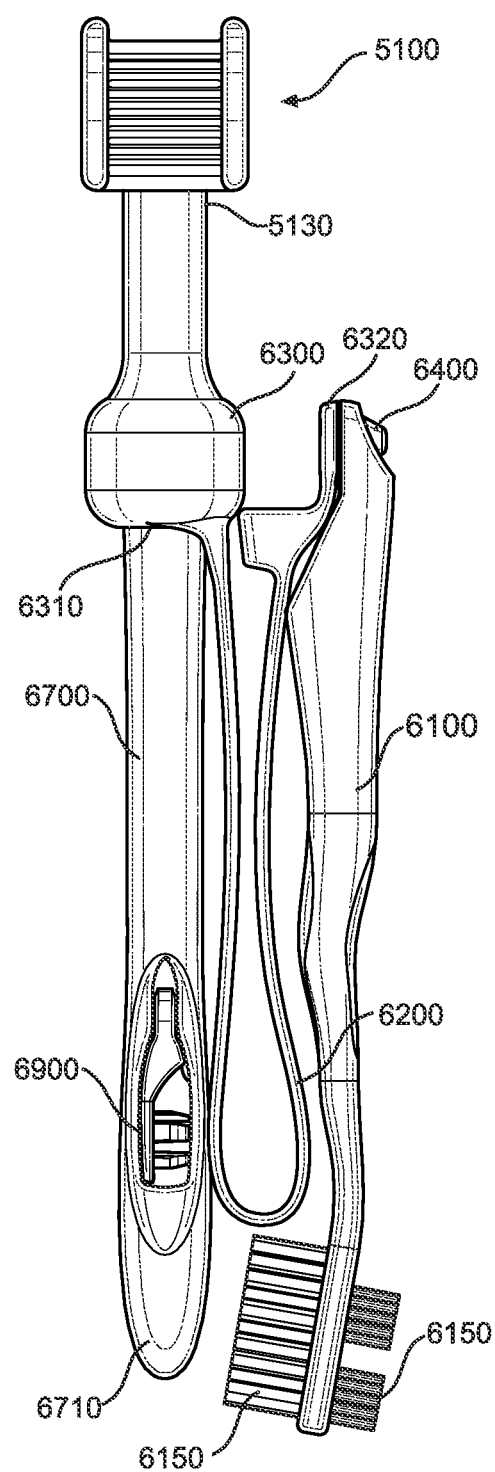
FIG. 8 shows a front view of a third embodiment of the dental bite block with a toothbrush attached.
Figure 9:
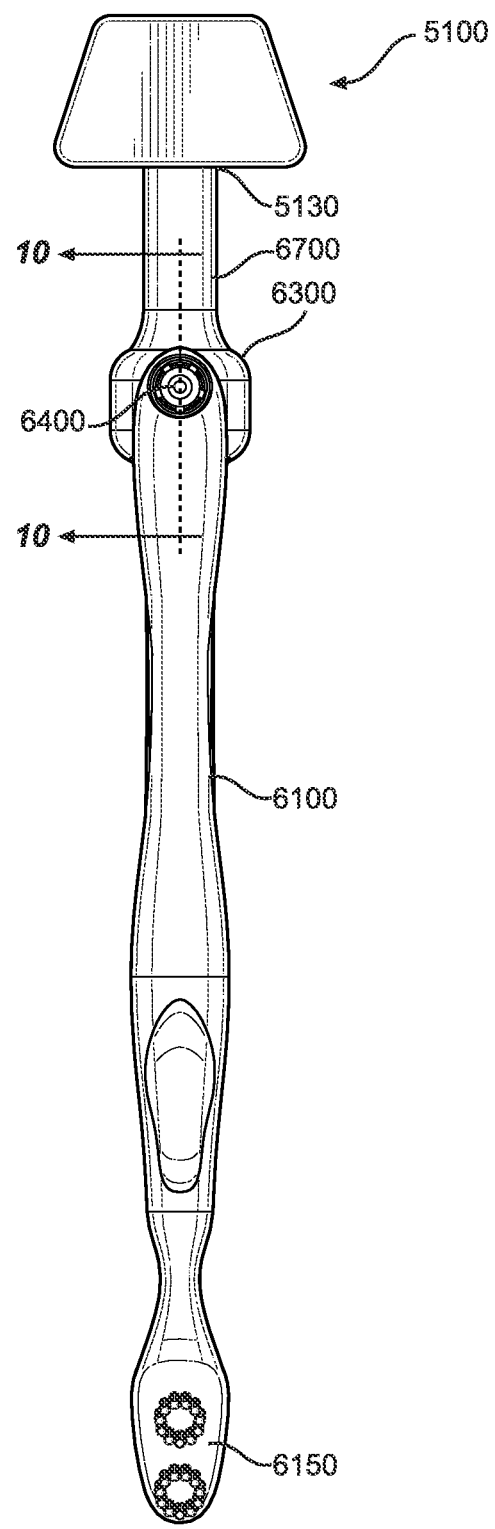
FIG. 9 shows a side view of the third embodiment of the dental bite block with a toothbrush attached.

Referring now to FIGS. 8 and 9, there is shown a front and side view of a third embodiment of the dental bite block with a toothbrush attached, respectively. In the shown embodiment, the handle 6700 extends from the second end 5130 of the body 5100, wherein the handle 6700 is axially aligned with a longitudinal axis of the body 5100 and adapted to be gripped by a user. A toothbrush 6100 is operably connected to the handle 6700 via a tether 6200. The tether 6200 is a flexible strap connected to an annular fastener 6300 at a first end 6310 and removably connected to the toothbrush 6100 via a releasable connector 6400 at a second end 6320, wherein the annular fastener 6300 is adapted to encircle the handle 6700 and freely rotate about a longitudinal axis of the handle 6700, wherein the longitudinal axis of the handle 6700 extends between the body 5100 and an opposing distal second end 6710.

In the shown embodiment, the toothbrush 6100 comprises bristles 6150 positioned at an end, wherein the bristles 6150 extend from both sides thereof. In one embodiment, the bristles 6150 only extend from a first side. As seen in FIG. 9, the bristles 6150 disposed on the second side of the toothbrush 6100 form a pair of subgroups of bristles, wherein these bristles in the subgroups form a circle having no bristles positioned within the circle. In an alternative embodiment, the subgroups of bristles may have any form and may or may not include individual bristles positioned within the form. In the shown embodiment on FIGS. 8 and 9, the tether 6200 arranges the toothbrush 6100 and the body 5100 such that each is oriented at opposing distal ends of the present invention. Additionally, the annular fastener 6300 is disposed intermediate the first end and an opposing distal second end of the handle 6700.

Figure 10:
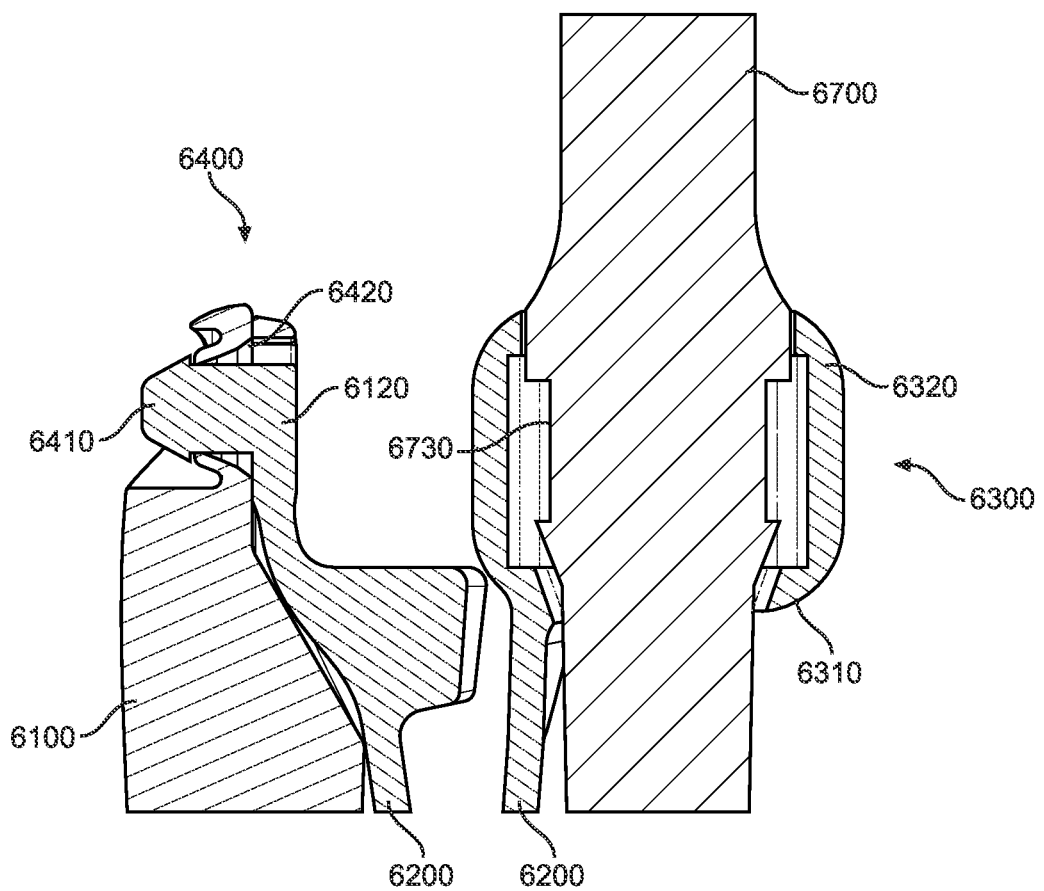
FIG. 10 shows a cross-sectional view of the annular fastener coupling the tether to the handle and the releasable connector coupling the tether to the toothbrush taken along line 10-10 of FIG. 9.

Referring now to FIG. 10, there is shown a cross-sectional view of the annular fastener coupling the tether to the handle and the releasable connector coupling the tether to the toothbrush taken along line 10-10 of FIG. 9. In the shown embodiment, the annular fastener 6300 extends from the tether 6300 and couples to the handle 6700. The annular fastener 6300 encircles the handle 6700 such that the annular fastener 6300 is adapted to rotate about the handle 6700. In one embodiment, the annular fastener 6300 includes a first member 6310 that secures directly to an annular recess 6730 of the handle 6700. A second member 6320 is slidably engaged to the first member, such that the second member is free to rotate thereabout. In one embodiment, the second member 6320 releases from the first member 6310 and a sufficient tension force is applied to the tether. For example, if the toothbrush 6100 is pulled away from the handle 6700, the annular fastener 6300 will temporarily uncouple. This provides safety to the user in the case of accidental pulling of the toothbrush during use. In other embodiments, the tether 6200 may release elsewhere to prevent the transfer of force therebetween.

Figure 11A:
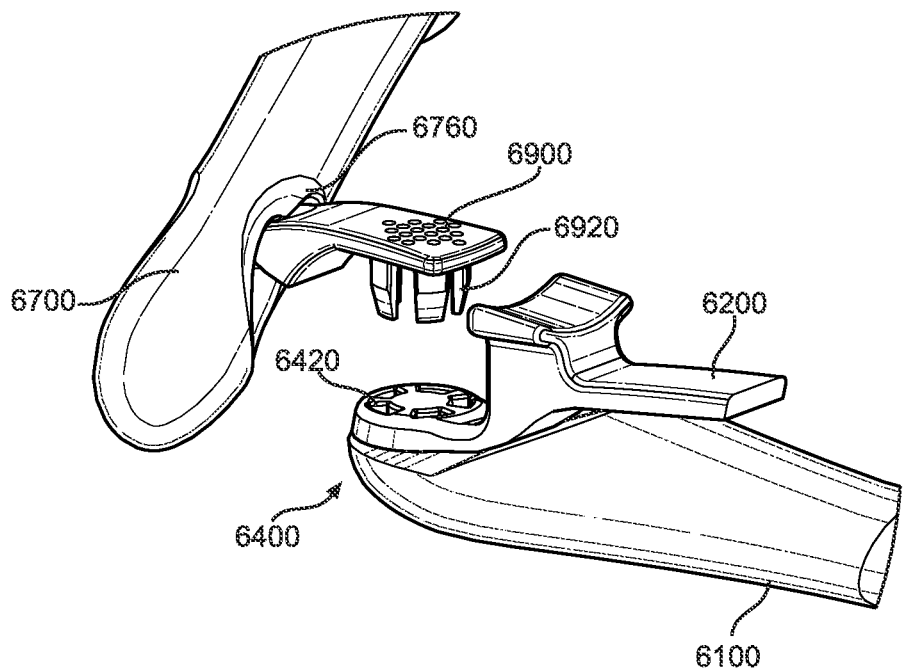
FIG. 11A shows a perspective view of the handle of the dental bite block coupled to the tether with a key in an in-use position.
Figure 11B:
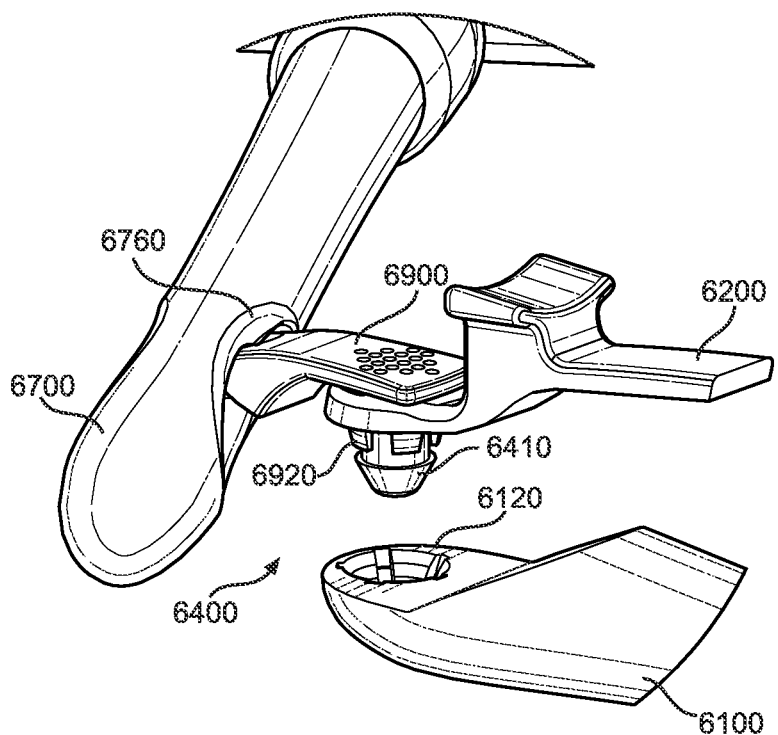
FIG. 11B shows a perspective view of handle of the dental bite block coupled to the tether and cooperatively decoupled from the toothbrush.

In the shown embodiment, the releasable connector 6400 of the tether 6200 comprises a tab 6410 adapted to frictionally and releasably engage with the toothbrush 6100 and one or more apertures 6420 adapted to receive a key (shown in FIGS. 11A and 11B). The key is adapted to decouple the tether 6200 from the toothbrush 6100. In the shown embodiment, the toothbrush 6100 comprises a channel 6120 disposed perpendicular to a longitudinal axis of the toothbrush 6100, wherein the channel 6120 is sized to releasably couple to the tether 6200 via the releasable connector 6300.

Referring now to FIGS. 11A and 11B, there is shown a perspective view of the handle of the dental bite block coupled to the tether with a key in an in-use position, and a perspective view of handle of the dental bite block coupled to the tether and cooperatively decoupled from the toothbrush. In the shown embodiment, the toothbrush 6700 comprises a channel 6120 disposed perpendicular to a longitudinal axis of the toothbrush, wherein the channel 6120 is sized to releasably couple to the tether 6200 via the releasable connector 6400.

In the shown embodiment, a key 6900 is operably connected to the handle 6100 and is movable between a retracted position (See FIG. 8) and an in-use position (See FIG. 11A, 11B). In the retracted position, the key 6900 is housed entirely within a slot 6760 of the handle. In this way, the key 6900 does not inhibit from the use and enjoyment of the present invention. In the in-use position, the key 6900 is removed from the slot 6760 such that the key 6900 is free to engage with the releasable connector 6400 to decouple the tether 6200 from the toothbrush 6100.

In one exemplary use, a user may selectively disconnect the toothbrush 6100 from the tether 6200. The toothbrush 6100 may be reconnected to the tether as desired, or a similar replacement toothbrush may take the position of the original toothbrush 6100. In FIG. 11A, the toothbrush 6100 and handle 6700 are connected as shown in FIG. 8. The key 6900 is rotated away from the slot 6760 of the handle 6700, such that protruding bits 6920 are positioned over the one or more apertures 6420. Once engaged, the key 6900 releases the tab 6410 from the channel 6120 and releasably couples to the key 6900 resulting in FIG. 11B.

Figure 12:
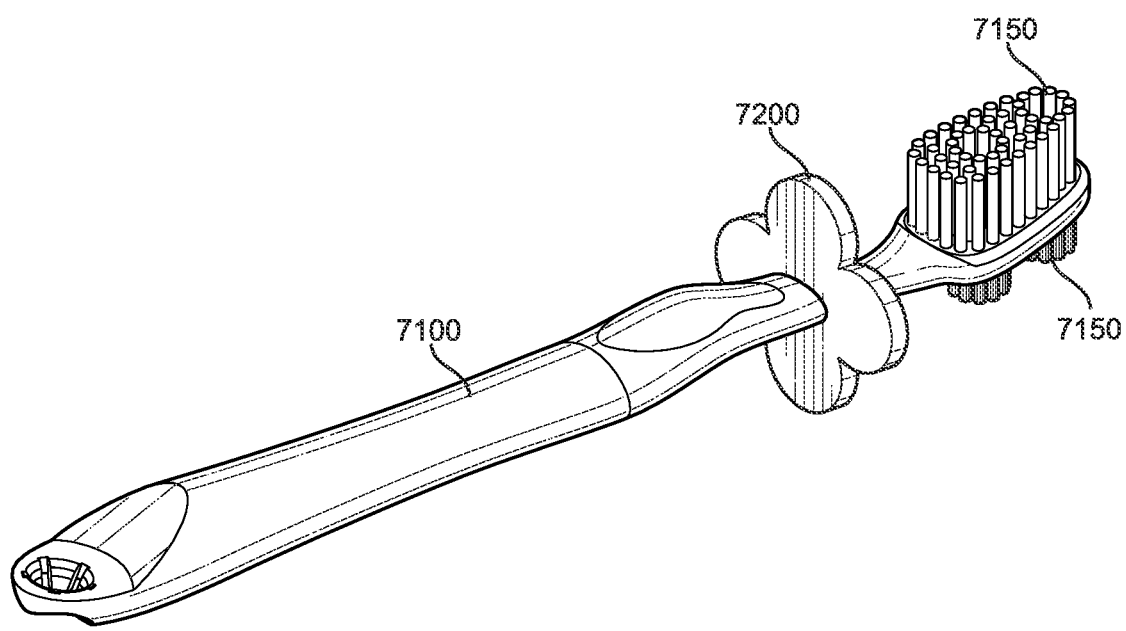
FIG. 12 shows a perspective view of a toothbrush of the dental bite block.

Referring to FIG. 12, there is shown a perspective view of an embodiment of the toothbrush of the dental bite block. In the shown embodiment, the toothbrush 7100 comprises an elongated member having one or more bristle groups 7150 located at an end. The toothbrush 7100 further includes a guard member 7200 positioned intermediate the one or more bristle groups 7150 and a gripping portion. In the shown embodiment, the toothbrush 7100 is sized for children. In alternative embodiments, the toothbrush 7100 comprises any size usable for men, women, children, pets, and the like.

It is therefore submitted that the instant invention has been shown and described in what is considered to be the most practical and preferred embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

We claim:

1. A dental bite block, comprising:
a body having a first end and a second end, wherein an outer sidewall and an inner sidewall are disposed on opposing sides thereof;
wherein the body comprises an upper biting surface positioned within an upper channel and a lower biting surface within a lower channel;
wherein the outer sidewall and the inner sidewall extend past the upper and lower biting surfaces and define the upper channel and the lower channel, respectively, wherein the upper channel and the lower channel are each adapted to receive a row of teeth therein;
wherein the body comprises a front face at the first end thereof, wherein the front face extends between the upper biting surface and the lower biting surface;
a handle extending from the second end of the body, wherein the handle is axially aligned with a longitudinal axis of the body and adapted to be gripped by a user;
wherein a toothbrush is operably connected to the handle via a tether;

wherein the tether comprises a flexible strap connected to an annular fastener at a first end of the flexible strap and removably connected to the toothbrush via a releasable connector at a second end of the flexible strap, wherein the annular fastener is adapted to encircle the handle and freely rotate about a longitudinal axis of the handle, wherein the longitudinal axis of the handle extends within the body at a first end of the handle and an opposing distal second end of the handle.

2. The dental bite block of claim 1, wherein the upper and lower biting surfaces each include a rib, the ribs adapted for aiding traction on the bite block by the upper and lower teeth.

3. The dental bite block of claim 2, wherein the rib comprises a plurality of ribs oriented perpendicular to a longitudinal axis of the upper channel and the lower channel, respectively.

4. The dental bite block of claim 1, wherein the upper biting surface and the lower biting surface are inclined towards the first end of the body.

5. The dental bite block of claim 1, wherein the outer and the inner sidewalls are inclined towards the first end of the body and the body being thicker at the second end thereof than at the first end thereof.

6. The dental bite block of claim 5, wherein the outer sidewall and the inner sidewall are inclined at a uniform slope.

7. The dental bite block of claim 1, wherein a width between the outer and inner sidewalls is uniform, and wherein there is a uniform height difference between sidewalls at a same cross section along a longitudinal axis of the body.

8. The dental bite block of claim 1, wherein the dental bite block is symmetrical about a horizontal plane disposed on a longitudinal axis of the body such that wherein a longitudinal axis of the upper channel and a longitudinal axis of the lower channel converge at a point disposed on the horizontal plane.

9. The dental bite block of claim 1, wherein the body is monolithic.

10. The dental bite block of claim 1, wherein an exterior side of the outer sidewall is planar and continuous entirely thereacross.

11. The dental bite block of claim 1, wherein the upper channel and the lower channel are open at the first end and the second end, respectively.

12. The dental bite block of claim 1, wherein the annular fastener is disposed intermediate the first end of the handle and the opposing distal second end of the handle.

13. The dental bite block of claim 1, wherein the releasable connector of the tether comprises a tab adapted to frictionally and releasably engage with the toothbrush and one or more apertures adapted to receive a key, the key adapted to decouple the tether from the toothbrush.

14. The dental bite block of claim 13, wherein the toothbrush comprises a channel disposed perpendicular to a longitudinal axis of the toothbrush, wherein the channel is sized to releasably couple to the tether via the releasable connector.

15. The dental bite block of claim 13, wherein the key is operably connected to the handle and is movable between a retracted position and an in-use position, wherein the retracted position the key is housed entirely within a slot of the handle, wherein the in-use position the key is removed from the slot such that the key is free to engage with the releasable connector to decouple the tether from the toothbrush.

16. The dental bite block of claim 1, wherein the toothbrush comprises bristles disposed on opposing sides thereof.

17. The dental bite block of claim 1, wherein the outer sidewall comprises a first height greater than a second height of the inner sidewall at a same cross section along a longitudinal axis of the body;
wherein the upper channel and the lower channel each form an acute angle relative to a longitudinal axis of the body;
wherein the acute angle is between fifteen and thirty degrees.

* * * * *